United States Patent [19]

Nonoyama et al.

[11] Patent Number: 5,643,881
[45] Date of Patent: Jul. 1, 1997

[54] PROTEIN HAVING ANTI-HIV ACTIVITY AND METHOD FOR OBTAINING IT

[75] Inventors: Meihan Nonoyama, St. Petersburg; Akiko Tanaka; Patrick K. Lai, both of Clearwater, all of Fla.

[73] Assignee: Tampa Bay Research Institute, St. Petersburg, Fla.

[21] Appl. No.: 285,436

[22] Filed: Aug. 4, 1994

[51] Int. Cl.$^6$ .................... A61K 38/17; C07K 14/435; C12P 21/00
[52] U.S. Cl. .................... 514/21; 435/70.4; 530/350
[58] Field of Search .................... 435/70.4, 70.5; 530/350, 351, 395, 380, 416, 420, 414; 514/2, 8, 12, 21

[56] References Cited

U.S. PATENT DOCUMENTS

| | | | |
|---|---|---|---|
| 4,683,199 | 7/1987 | Palladino | 435/172.2 |
| 5,039,794 | 8/1991 | Wier et al. | 530/399 |
| 5,149,785 | 9/1992 | Cantor et al. | 530/350 |
| 5,157,112 | 10/1992 | Van Snick et al. | 530/351 |
| 5,236,829 | 8/1993 | Farber | 435/69.1 |
| 5,292,636 | 3/1994 | Kung et al. | 435/7.9 |
| 5,346,988 | 9/1994 | Nonoyama et al. | 530/300 |

FOREIGN PATENT DOCUMENTS

| | | |
|---|---|---|
| 0143850 | 6/1985 | European Pat. Off. |
| 0193032 | 9/1986 | European Pat. Off. |
| 0296626 | 12/1988 | European Pat. Off. |
| 0310056 | 4/1989 | European Pat. Off. |
| 2146645 | 4/1985 | United Kingdom. |

OTHER PUBLICATIONS

Lai et al., *AIDS Research and Human Retroviruses*, 6:205–217 (1990).
Shinazi et al., *Antimicrob. Agents Chemother.*, 34:1061–1066 (1990).
Cooley et al., *New England J. of Med.*, 322:1340–1345 (1990).
Harris et al., "Protein purification methods", 1989, IRL Press, pp. 9–10 and 57–60.
Harris et al., Protein purification methods, published 1989 by IRL Press (New York), pp. 126, 127, 139, 142.
Science, vol. 238, issued 18 Dec. 1987, Smith et al, "Blocking of HIV–1 Infectivity by a Soluble...", pp. 1704–1707.

*Primary Examiner*—Jeffrey E. Russel
*Attorney, Agent, or Firm*—Rothwell, Figg, Ernst & Kurz

[57] ABSTRACT

A protein having potent anti-HIV activity is obtained by a method which comprises culturing a strain of CD4-positive T cells, such as a subclone of CEM cells designated 4084, in a tissue culture medium under conditions in which the cells are induced to produce and secrete a protein having anti-HIV activity, separating the cells from the culture medium containing the protein and then recovering the protein from the medium, wherein the molecular weight of the protein having anti-HIV activity is at least 30,000 daltons as determined by a membrane with defined pore size that retains molecules of 30,000 daltons.

14 Claims, No Drawings

PROTEIN HAVING ANTI-HIV ACTIVITY AND METHOD FOR OBTAINING IT

FIELD OF THE INVENTION

This invention is directed to protein produced and secreted from human CD4-positive T cells which has potent anti-HIV activity.

BACKGROUND OF THE INVENTION

Acquired Immune Deficiency Syndrome (AIDS) has become a significant public health threat in recent years. A major breakthrough in AIDS research came in 1983–1984 when two groups independently isolated and identified a virus believed to be the causative agent of AIDS. The AIDS virus has been described by several names. It has been known as lymphadenopathy-associated virus (LAV), AIDS-related virus (ARV) and human immunodeficiency virus (HIV). Within the last few years, scientists have discovered that there are at least two distinct viruses, HIV-1 and HIV-2. HIV-1 is the virus originally isolated in 1983 (*Ann. Virol. Inst. Pasteur,* 135E:119–134 [1986]); HIV-2 was isolated by researchers in 1986 (see *Nature,* 326:662 [1987]). As used herein, HIV refers to these viruses generically.

A distinguishing feature of HIV is its selective cytotoxicity for helper T lymphocytes. The virus also infects monocytes/macrophages, B lymphocytes and neural cells. Severe and diverse aberrations of the immune system significantly reduce the host defense against various opportunistic infections, ultimately resulting in host death.

There are a number of proteins secreted by human cells that can regulate the human immune system. These secreted proteins with regulatory activities generally are classified as interleukins or cytokines. The United States Food and Drug Administration (FDA) has approved the use of some of the interleukins/cytokines in clinical trials for the treatment of AIDS. Those approved for clinical trials include interleukin-2 (IL-2), tumor necrosis factor-alpha (TNF-α), interferon-alpha (INF-α), interferon-beta (INF-β), interferon-gamma (INF-γ) and colony stimulating factor for granulocytes and macrophages (GM-CSF). Only the interferons have been shown to possess anti-viral activities before the initiation of the clinical trials. The high doses of interferon required in treatment often give undesirable short-term side effects that precipitate the withdrawal of the interferon treatment. IL-2 has shown no anti-HIV activity, and data available thus far suggest that IL-2 has no significant impact on the reconstitution of CD4-positive helper T cell populations in AIDS patients. Recent reports also have shown that TNF-α and GM-CSF can activate latent HIV in cells maintained in tissue culture. Thus, it is questionable if these agents can be used long-term to treat AIDS patients. There thus remains an urgent need for methods of inactivating the AIDS virus and for the treatment of AIDS.

It therefore is an object of the present invention to provide a novel protein having potent anti-HIV activity. It is a further object of the invention to provide a protein which can substantially inhibit the replication of HIV in HIV-infected cells. Other objects of the invention will become apparent from the following description.

SUMMARY OF THE INVENTION

In accordance with the present invention, there is provided a method for obtaining a soluble protein, or proteins, having potent anti-HIV activity, secreted by a CD4-positive T cell line cultured in a tissue culture medium. The soluble protein, or proteins, with potent anti-HIV activity, as determined by retention by membrane with a defined pore size, has a molecular weight of at least about 30,000 daltons.

The protein, or proteins, can be recovered from the cell culture by first separating the cells from the medium. The resultant cell-free solution is passed through a 30 kDa molecular sieve and the fraction containing molecules having a molecular weight of at least about 30,000 is collected. The preparation has potent anti-HIV activity and can be purified further by first passing it through a cation exchange column and then an ion exchange column and collecting the fraction(s) which possess anti-HIV activity.

DETAILED DESCRIPTION OF THE INVENTION

Commonly-assigned U.S. Pat. 5,346,988 incorporated by reference, teaches obtaining a protein having potent anti-HIV activity by cultivating CD4-positive T cells in the presence of an activating agent and recovering from the culture medium a protein having a molecular weight in the range of 7,000 to 12,000 daltons. Applicants now have discovered that in addition to this protein, a larger protein, having a molecular weight of at least 30,000 daltons, which also has strong anti-HIV activity, also can be produced.

Suitable starting material for the process of this invention is a CD4-positive T cell line, such as CEM, available from the American Type Culture Collection (ATCC), Rockville, Md., accession number CCL119. Cells from the CEM cell line were sub-cloned in microtiter wells as described in example 1 below. One subclone was designated Clone 4084 and a cell sample was deposited with the ATCC on Aug. 3, 1994, in accordance with the provisions of the Budapest Treaty and accorded accession number 11697.

To obtain the protein with a molecular weight of at least 30 kDa having anti-HIV activity, cells from clone 4084 are cultured in a tissue culture medium. Generally, any commercially available medium is acceptable to support the growth of the cells, such as RPMI-1640, commercially available from Media Tech., Herndon, Va. Desirably, the medium is supplemented with 5% v/v fetal bovine serum, 100 units/ml penicillin and 100 µg/ml streptomycin.

The culture medium also is modified by the addition of an agent suitable for activating the cells. Examples of useful activating agents include PC6, an extraction from cones of conifer trees described by Lai et al., *AIDS Research and Human Retroviruses,* 6:205–217 (1990), alkaline aqueous extracts from cones of conifer trees (*Anticancer Research* 7:1153–1160 (1987), Klason lignin extracted from conifer cones or pulp waste (*Methods of Wood Chemistry,* B. L. Browning [ed.] Vol. II, p785, Interscience Publishers, N.Y.), alkaline lignin (Tokyo Kasei Organic Chemicals, Tokyo, Japan), de-alkaline lignin (Tokyo Kasei) and lignin sulfonate (Tokyo Kasei).

Generally, the activating agent is added to the tissue culture medium at a concentration of from about 1 to about 30 µg/ml of medium. The cells then are seeded at a concentration ranging from about $1 \times 10^5$ to about $6 \times 10^5$ cells/ml of medium.

The cells then are incubated, generally for a period of about 1 to about 7 days, under conditions which induce the cells to produce one or more proteins having anti-HIV activity. Generally, such conditions include an incubation temperature of about 37° C. and a 100% humidified atmosphere of about 5% carbon dioxide. The length of the incubation time has not been found to be critical; under the conditions generally described above, the cells produce the desired proteins within about 24 hours of the start of the incubation, and high levels of protein still are detected in the medium after 7 days of incubation.

To recover the anti-HIV proteins, the cells are separated from the aqueous medium. Typically, this is done by centrifugation at, for example, 800×g. The cell pellet is removed from the cell-free aqueous phase. The anti-HIV proteins are in the aqueous phase.

Throughout the remainder of the application, reference will be made to a relatively large protein and to a smaller protein, each of which has anti-HIV activity. It is to be recognized, however, that in fact what is produced and secreted by the cells may be a mixture of at least two proteins within each of the molecular weight ranges disclosed herein.

The supernatant containing the anti-HIV protein is passed through a 30 kDa molecular sieve. General conditions include a pressure of 18 psi or 500×g. Applicants have found that anti-HIV protein molecules are retained by this sieve. In addition, protein molecules which pass through this sieve but are retained with a 3 kDa molecular sieve also have anti-HIV activity. Thus, this is suggestive that the cells produce at least one protein having a molecular size which is at least about 30,000 daltons, as well as at least one protein having a molecular size between about 3,000 and 30,000 daltons. By gel filtration analysis, using high performance liquid chromatography, the molecular weight of the smaller protein has been determined to be within the range of about 7,000 to about 12,000 daltons relative to the gel filtration profile of molecular weight markers.

When cells infected with HIV are incubated in supernatant containing either the large or small anti-HIV protein, HIV replication is inhibited. When infected cells are contacted with the large protein, HIV replication is inhibited by more than 80%; when the cells are contacted with the smaller protein, replication also is inhibited by at least 80%. The large protein can inhibit HIV replication in T-cells by over 90%, and desirably by over 95%. The degree of inhibition of HIV replication in myeloid cells, such as U937 cells, typically is lower per given amount of protein than is observed in T-cells. HIV inhibitions in myeloid cells typically varies between about 60 and 80%.

Analysis of the large and small anti-HIV proteins produced in accordance with this method shows that neither is interleukin-1, interleukin-2, interleukin-3, interleukin-4, interleukin-5, interleukin-6, interleukin-7, interleukin-8, colony stimulation factor for granulocyte and macrophages (GM-CSF), colony stimulation factor for granulocytes, colony stimulation factor for macrophages, interferon-alpha, interferon-beta, interferon-gamma, tumor necrosis factor-alpha, tumor necrosis factor-beta, or transforming growth factor-beta. Specific neutralizing antibodies to each of these factors fails to abrogate the anti-HIV activity of a medium comprising either protein.

If desired, the large anti-HIV protein can be purified by ion exchange chromatography. Conventional liquid chromatography, high performance liquid chromatography, or fast performance liquid chromatography can be used. More specifically, to purify the large protein, that fraction of the supernatant which contains the large protein is added to an elution buffer to adjust the pH to be within the range of about 4.5 to about 5.6. A suitable elution buffer is 20 mM sodium acetate at pH 5.6, 10% glycerol, 0.1 mM of disodium salt of ethylene diamine tetraacetic acid (EDTA) at pH 6.0 and 0.1 mM dithiothreitol. The solution containing the anti-HIV protein is added to a cation exchange column, such as a CM-cellulose or mono-S column. The flow-through fraction from this column contains the majority of the large molecular weight anti-HIV protein. The pH of this fraction then is adjusted to be within the range of about 6.5 and about 7.8 in elution buffer. A suitable elution buffer is 20 mM Tris[hydroxymethyl] aminomethane at pH 7.4, 0.1 mM of disodium salt of ethylene diaminetetraacetic acid (EDTA) at pH 7.0, 10% glycerol, and 0.1 mM of dithiothreitol. The solution containing the anti-HIV protein is added to an anion exchange column, such as a DEAE or mono-Q column. The anion exchange column then is eluted with the elution buffer containing 1 M sodium chloride. The eluate contains the relatively large anti-HIV protein.

The large anti-HIV protein in aqueous solution can be stored at 4° C. for up to about 4 weeks.

The amount of protein preparation needed to inhibit HIV replication in vitro in HIV infected cells will vary depending upon the degree of purification of the protein. Typically, however, if the HIV-infected cells are cultured in a medium comprising the crude protein (i.e., protein obtained by passing the protein-containing supernatant through a 30 kDa molecular sieve) about 1 to about 5 mg of protein per ml. are sufficient to obtain at least 80% HIV inhibition. If the protein to be used has been purified by passing it through cation and anion exchange columns, typically only about 10 to about 50 µg of protein per ml. are needed to obtain at least 80% HIV inhibition. Useful amounts of protein from any given preparation can be determined readily by one of ordinary skill in the art once he has determined the activity of the protein and the total amount of protein present in the preparation.

The present invention is further illustrated by the following examples, which are not intended to be limiting.

EXAMPLE 1

Preparation of Clone 4084

CEM cells at $1.5 \times 10^5$ cells/ml were cultured at 37° C. for 2 days in 50 ml of RPMI-1640 tissue culture medium supplemented with 5% fetal bovine serum, 100 units/ml penicillin, 100 µg/ml streptomycin. The cells then were adjusted to $3 \times 10^6$ cells/ml with fresh medium. One ml of this cell suspension was added to 9 ml of fresh medium to give $3 \times 10^5$ cells/ml. After thorough mixing, 1 ml of this cell suspension again was added to 9 ml of fresh medium. This 10-fold dilution step was repeated serially to give a cell suspension containing 3 cells/ml. 100 µl of this cell suspension then were added to each well in a 96 well flat-bottomed tissue culture plate to give a frequency of 1 cell every three wells. A total of 20 tissue culture plates were seeded with this cell suspension. The plates were at 37° C. and in a humidified atmosphere of 5% $CO_2$. Wells in each plate were examined for signs of cellular proliferation every other day by use of an inverted microscope. At weekly intervals, 50 µl of fresh medium were added to each well to maintain the cells in culture. The plates were incubated for three weeks or when signs of proliferation were evident. Actively proliferating cells in each microwell then were transferred into wells in a 24 well flat-bottomed tissue culture plate. Each of these cloned cell cultures then were further expanded to 10 ml cultures in tissue culture flasks. One of the cloned cultures, clone 4, was recloned at 1 cell every three wells in flat-bottomed 96 well tissue culture plates as described above and again gave a large number of subclones. One of these, clone 4084, was a good producer of proteins having anti-HIV activity (see example 2, below).

EXAMPLE 2

Production of Proteins Having anti-HIV Activity

Clone 4084 cells were cultured at 37° C. for 2 days in 13,000 ml. of RPMI-1640 tissue culture medium supplemented with 5% fetal bovine serum, 100 units/ml of penicillin, 100 µg/ml streptomycin and 10 µg/ml PC6

(obtained from Tampa Bay Research Institute, St. Petersburg, Fla.). The cells were cultivated in 100% humidified atmosphere of 5% $CO_2$. The clone 4084 cells were removed from the culture medium by centrifugation at 800×g for 10 minutes and subsequent removal of the resultant cell pellet.

The supernatant was passed through a 30 kDa molecular sieve, spiral filtration cartridge, type S10Y30 (Amicon, Beverly, Mass.). The retentate contained the large protein with anti-HIV activity. The effluent was collected and allowed to pass through a 3 kDa molecular seive S10Y3 (Amicon). The retentate collected contained the small protein with anti-HIV activity.

To determine the anti-HIV activity of the large and small proteins, the following procedure was used:

The chloramphenicol acetyl-transferase (CAT) gene was introduced into HIV-1 (Langhoff, E. et al., *PNAS USA* 88:7998–8002 (1991). Expression of CAT was under the control of the HIV-1 promoter that controls the expression of all HIV-1 genes. Expression of CAT under the control of the HIV-1 promoter is a good measure of HIV-1 replication (Id.). CEM cells were infected with this recombinant HIV-1 by adding $1×10^6$ cells to each 1 ml of the virus.

The infected cells then were placed in RPMI-1640 medium supplemented with 2% heat-inactivated newborn calf serum, 100 units/ml of penicillin, 100 µg/ml streptomycin and varying dilutions (1 in 5 to 1 in 500) of one of the three protein preparations shown in Table 1. After incubation for 3 days, the amount of HIV-1 produced by the cells was measured by quantitation of CAT activity in each culture. CAT activity was measured by a mixed phase assay (Nielson, D. A., et al., *Analyt. Biochem.* 179:19–23 [1989]), wherein the ability to incorporate tritiated-acetyl group from tritiated acetyl Co-A onto chloramphenicol was quantitated in a liquid scintillation counter. Percent inhibition of HIV-1 replication was calculated from:

[(P−B)/(C−B)]×100 where P=CAT activity quantitated as counts per minute per microgram protein from infected cell culture treated with the protein preparation, C=CAT activity quantitated as counts per minute per microgram of protein from infected cell culture not treated with the protein preparation, and B is the background control given tritiated acetyl Co-A in the absence of chloramphenicol.

The results are shown in Table 1.

TABLE 1

| | Inhibition (%) of HIV-1 by | | |
|---|---|---|---|
| Sample Dilutions+ | Supernatant from Stimulated 4084 cells | Fraction through passed 30 kDa sieve, but retained by 3 kDA sieve | Fraction retained by the 30 kDA sieve |
| 1 in 5 | 80% | 83% | 97% |
| 1 in 25 | 65% | 65% | 94% |
| 1 in 100 | 55% | 21% | 81% |
| 1 in 500 | N.T. | N.T. | 34% |
| Units/ml* | 100 | 40 | 350 |
| Total Units** | 110,000 | 36,000 | 70,000 |

*one unit is defined as the amount of protein required to inhibit HIV-1 replication by 50%.
**total unit is given by Units/ml × total volume of protein preparation
+the samples were concentrated 10 x before testing in the varying dilutions listed below.

EXAMPLE 3

Inhibition of HIV Replication in U937 Cells

The following experiment was designed to show HIV-1 replication in U937 myeloid cells could be inhibited by the large protein.

CEM cells (ATCC Accession No. CCL119) or U937 cells (ATCC Accession No. CRL1593) were infected with the recombinant HIV-1 as described in Example 2, above. These infected cells then were placed in RPMI-1640 medium supplemented with 2% heat inactivated newborn calf serum, 100 units/ml penicillin, 100 µg/ml streptomycin and a 1 in 10 dilution of the protein preparation retained by the 30 kDa molecular sieve. After incubation for 3 days, the amount of HIV-1 produced was measured by quantitation of CAT activity in each culture. CAT activity was measured by a mixed phase assay as described in the preceding example, wherein the ability to incorporate tritiated-acetyl group from tritiated acetyl Co-A onto chloramphenicol was quantitated in a liquid scintillation counter. Percent inhibition of HIV-1 was calculated as described in the preceding example. The results are set forth in Table 2.

TABLE 2

| | Percent inhibition of HIV-1 replication in | |
|---|---|---|
| | CEM cells | U937 cells |
| HIF Fraction retained by 30 kDA sieve tested at 1 in 10 dilution | 85% | 64% |

EXAMPLE 4

Purification of Protein with Anti-HIV Activity

Clone 4084 cells were cultured at 37° C. for 2 days in 13.8 liters of RPMI-1640 tissue culture medium, supplemented with 5% fetal bovine serum, 100 units/ml penicillin, 100 µg/ml streptomycin and 10 µg/ml PC6. The cells were cultivated in 100% humidified atmosphere of 5% $CO_2$. The cells were removed by centrifugation, the fraction that could be retained by the 30 kDa molecular seive and contained the large protein with anti-HIV activity was prepared as described in Example 2. The volume of this fraction was 3.3 liters. If one defines one unit (U) of anti-HIV activity as the amount of protein needed to inhibit HIV replication by 50% in 1 ml culture of infected CEM cells, this fraction would have 10 U/ml or approximately 33,000 U of total anti-HIV activity (Table 3). This fraction was added to an equal volume of acetate elution buffer [20 mM sodium acetate at pH 5.6, 10% glycerol, 0.1 mM disodium salt of ethylene diamine tetraacetic acid (EDTA) at pH 6.0 and 0.1 mM dithiothreitol]. The volume of this mixture was reduced to 3.3 liter by passing it through a 30 kDa membrane (type S10Y30, Amicon) at 18 psi or 500×g. This washing procedure was repeated 5 times to equilibrate this fraction with the acetate elution buffer. The equilibrated fraction then was added to CM-cellulose. Fractions that flowed through CM-cellulose were collected (3.3 liters). Material bound to CM-cellulose was recovered by a single step elution with 0.3M NaCl in acetate elution buffer. As shown in Table 3, a total of 900 U were found in the 0.3M NaCl eluted fraction, whereas the CM-flow-through fraction has approximately 33,000 U. If one defines anti-HIV specific activity as the units of anti-HIV activity present in 1 mg of proteins, i.e. total anti-HIV units in a fraction divided by total proteins in mg in the fraction, the 0.3 M NaCl eluted fraction has a specific activity of 0.6, while the CM-flow-through fraction had a specific activity of 4.17.

The CM-flow-through fraction containing the large protein having anti-HIV activity that did not bind to CM-cellulose at pH 5.6 then was adjusted to pH 7.4 by the addition of Tris[hydroxymethyl] aminomethane and added to DEAE cellulose. The fraction that flowed through the DEAE-cellulose was collected. Material bound to DEAE-cellulose was recovered by stepwise elution with 0.3 M and 1.0 M NaCl in elution buffer of 20 mM Tris[hydroxymethyl] aminomethane at pH 7.4, 10% glycerol, 0.1 mM disodium salt of EDTA at pH 7.0 and 0.1 mM dithiothreitol. When tested for anti-HIV activity, the fraction that flowed through DEAE-cellulose and contained material not bound to DEAE-cellulose did not have anti-HIV activity. The 0.3 M NaCl eluted fraction had 2400 U of anti-HIV activity but with a specific activity of 0.87. In contrast, the 1.0 M NaCl eluate had 6000 U of anti-HIV activity and a specific activity of 95 (Table 3).

TABLE 3

Amount of anti-HIV activity in

| | Units*/ml | Total U** | Specific Activity*** (U/mg) |
|---|---|---|---|
| Fraction retained by 30 kDa molecular sieve | 10 | 33,000 | 0.88 |
| Fraction recovered by 0.3 M NaCl elution from the CM-cellulose | 3 | 900 | 0.66 |
| Fraction not bound to the CM-Cellulose at pH 5.6 | 10 | 33,000 | 4.17 |
| Fraction not bound to the CM-cellulose, and also not bound to DEAE-cellulose at pH 7.4 | 0 | 0 | 0 |
| Fraction not bound to the CM-cellulose, but bound to DEAE-cellulose and eluted by 0.3 M NaCl | 4 | 2,400 | 0.87 |
| Fraction not bound to the CM-cellulose, but bound to DEAE-cellulose and eluted by 1.0 M NaCl | 15 | 6,000 | 95.0 |

*One unit (U) is defined as the amount of HIF required to inhibit HIV-1 replication by 50%
**Total units is given by U/ml × total volume of an HIF preparation
***Specific activity (U/mg) is given by total U in an HIF preparation divided by the total amount of protein (mg) present in that HIF preparation.

What is claimed is:

1. A method for obtaining a protein having anti-HIV activity which comprises:
   (a) culturing CD4-positive T cells deposited with the ATCC as accession number 11697 in a tissue culture medium which comprises an agent to activate the cells comprising PC6, alkaline lignin, de-alkaline lignin or lignin sulfonate under conditions in which the cells are induced to produce and secrete at least one protein soluble in the culture medium having anti-HIV activity,
   (b) separating the cells from the culture medium containing the protein having anti-HIV activity, and
   (c) recovering the protein from the medium, wherein the protein is characterized by a molecular weight of at least about 30,000 daltons.

2. The method of claim 1, wherein the cells are seeded in the culture medium at a concentration of about $1 \times 10^5$ cells/ml to about $6 \times 10^5$ cells/ml and the activating agent is provided at a concentration of from about 1 µg/ml to about 30 µg/ml.

3. The method of claim 2, wherein the cells are grown for about 1–7 days.

4. The method of claim 1, wherein the culture medium further comprises V/V 5% fetal bovine serum, 100 units/ml penicillin and 100 µg/ml streptomycin.

5. The method of claim 1, wherein the protein having anti-HIV activity is recovered from the culture medium by passing the medium containing the anti-HIV protein through a 30 kDa molecular sieve and retaining that portion which does not pass through the sieve.

6. The method of claim 5, wherein the anti-HIV protein in the retained portion of the medium is precipitated from the medium by adding a supersaturated aqueous solution of ammonium sulfate to the medium.

7. The method of claim 6, wherein the anti-HIV protein is purified by adjusting the pH of the retained portion of the medium to be within the range of about 4.5 to about 5.6, then loading it onto a cation exchange column and collecting the flow-through fraction from the column.

8. The method of claim 7, which further comprises adjusting the pH of the flow-through fraction of the cation exchange column to be within the range of about 6.5 and 7.8 in elution buffer, loading the pH-adjusted flow-throught fraction onto an anion exchange column, eluting the column with an elution buffer containing sodium chloride, and recovering the resulting eluate.

9. The method of claim 1, wherein the activating agent comprises PC6.

10. A method for inhibiting HIV replication in vitro which comprises contacting cells infected with HIV with a protein which inhibits HIV replication in cells infected with HIV in an amount sufficient to, inhibit HIV replication, wherein the protein can be produced by
    (a) culturing CD4 positive T cells deposited with the ATCC as accession number 11697 in a tissue culture medium comprising an agent to activate the cells;
    (b) incubating said tissue culture medium for a period of time sufficient to induce said cells to produce a protein having anti-HIV activity;
    (c) separating the cells from the culture medium containing the protein having anti-HIV activity; and
    (d) recovering the protein from the medium by passing the medium containing the anti-HIV protein through a 30 kDa molecular sieve and retaining that portion which does not pass through the sieve, wherein the protein is characterized by a molecular weight of at least 30,000 daltons.

11. A method in accordance with claim 10, wherein the activating agent comprises PC6, alkaline lignin, de-alkaline lignin or lignin sulfonate.

12. A method in accordance with claim 10, wherein the HIV-infected cells are cultured in a medium containing between 10 µg. per ml. of the protein and 5 mg. per ml.

13. A method in accordance with claim 12, wherein HIV replication is inhibited by at least about 80%.

14. A method in accordance with claim 13, wherein HIV replication is inhibited by at least about 90%.

* * * * *